United States Patent
Chen et al.

(10) Patent No.: US 11,185,563 B2
(45) Date of Patent: Nov. 30, 2021

(54) METHOD AND COMPOSITION FOR PREVENTING, TREATING OR RELIEVING BONE DISEASES

(71) Applicant: GRAPE KING BIO Ltd., Taoyuan (TW)

(72) Inventors: Chin-Chu Chen, Taoyuan (TW); Yen-Lien Chen, Taoyuan (TW); Shin-Wei Lin, Taoyuan (TW); Yen-Po Chen, Taoyuan (TW); Yang-Tzu Shih, Taoyuan (TW); Ching-Wen Lin, Taoyuan (TW)

(73) Assignee: GRAPE KING BIO Ltd., Taoyuan (TW)

( * ) Notice: Subject to any disclaimer, the term of this patent is extended or adjusted under 35 U.S.C. 154(b) by 140 days.

(21) Appl. No.: 16/391,777

(22) Filed: Apr. 23, 2019

(65) Prior Publication Data

US 2019/0321420 A1    Oct. 24, 2019

(30) Foreign Application Priority Data

Apr. 24, 2018  (TW) .................. 107113917

(51) Int. Cl.
| | |
|---|---|
| *A61K 35/747* | (2015.01) |
| *A23L 33/135* | (2016.01) |
| *A61K 47/42* | (2017.01) |
| *A61K 47/26* | (2006.01) |
| *A61K 47/36* | (2006.01) |
| *A61P 19/10* | (2006.01) |
| *A61K 9/00* | (2006.01) |

(52) U.S. Cl.
CPC .......... *A61K 35/747* (2013.01); *A23L 33/135* (2016.08); *A61K 9/0053* (2013.01); *A61P 19/10* (2018.01); *A23V 2002/00* (2013.01); *A23V 2200/306* (2013.01); *A23Y 2220/63* (2013.01); *A23Y 2220/67* (2013.01); *A61K 47/26* (2013.01); *A61K 47/36* (2013.01); *A61K 47/42* (2013.01)

(58) Field of Classification Search
CPC ..... A61K 35/747; A61P 19/10; A23L 33/135; A23Y 2220/63; A23Y 2220/67
See application file for complete search history.

(56) References Cited

U.S. PATENT DOCUMENTS

2016/0067289 A1* 3/2016 Berggren .................. C12R 1/25
424/93.45

OTHER PUBLICATIONS

Collins et al., "The potential of probiotics as a therapy for osteoporosis" Microbiol Spectr, (Year: 2017).*
Govender et al., "Formulation Advancements in Probiotic Delivery" (PharmSciTech, 2013, vol. 14, No. 1, p. 29-43) (Year: 2013).*
Kechagia et al., "Health Benefits of Probiotics: A Review" (ISRN Nutrition, 2013, p. 1-7) (Year: 2013).*

* cited by examiner

*Primary Examiner* — Ruth A Davis
(74) *Attorney, Agent, or Firm* — Volpe Koenig

(57) ABSTRACT

The present invention discloses uses of treating, preventing or improving bone diseases by *Lactobacillus* or a composition including the *Lactobacillus*. The *Lactobacillus* and compositions can increase the blood calcium concentration, the trabecular bone volume density, the trabecular thickness, the trabecular number and the bone mineral density of a subject, and reduce trabecular spacing of the subject. Further, the present invention discloses a method for treating a subject diagnosed with a bone disease, through identifying the subject having the bone disease and administering to the subject an effective amount of a composition including at least one of *Lactobacillus plantarum* GKM3 and *Lactobacillus paracasei* GKS6, wherein the *Lactobacillus plantarum* GKM3 is deposited in China General Microbiological Culture Collection Center (CGMCC) with a deposition number of CGMCC 14565 on Aug. 25, 2017, and the *Lactobacillus paracasei* GKS6 is deposited in CGMCC with a deposition number of CGMCC 14566 on Aug. 25, 2017.

20 Claims, 3 Drawing Sheets

METHOD AND COMPOSITION FOR PREVENTING, TREATING OR RELIEVING BONE DISEASES

CROSS-REFERENCE TO RELATED APPLICATION AND CLAIM OF PRIORITY

This application claims the benefit of the Taiwan Patent Application No. 107113917, filed on Apr. 24, 2018, at the Taiwan Intellectual Property Office, the disclosures of which are incorporated herein in their entirety by reference.

FIELD OF THE INVENTION

The invention relates to the use of *Lactobacillus*, in particular, the use of *Lactobacillus* in preparing an edible composition and a pharmaceutical composition for treating, preventing or relieving bone diseases.

BACKGROUND OF THE INVENTION

Population aging is a global phenomenon, and age-related diseases are increasing day by day, which is a concern for governments and health professionals in all countries. One age-related category is bone diseases, such as osteoporosis, bone defects, bone fractures, and so on.

Osteoblasts, osteoclasts, and osteocytes are all related to bone development. Osteoblasts (also known as bone forming cells) are cells with a single nucleus for synthesizing bone matrix. Osteoclasts are multinucleated giant cells responsible for dissolution and absorption of bone. Generally, bone mass density (BMD) peaks at about 30~35 years of age. Bone mineral density decreases with age at a rate of 0.5% to 1% per year, particularly at a rate of 1~3% per year after the age of 50. The average rate of bone loss during menopause is about 1% per year. About 40% of menopausal women may suffer from osteoporosis. Menopausal women are prone to losing bone during menopause because of significantly decreased estrogen levels and increased osteoclast levels, which may cause catheter compression, or hip and wrist fractures.

Targeted bone remodeling through the activities of osteoblasts (bone forming cells) and osteoclasts (bone resorbing cells) maintains blood calcium concentrations within a critical range while keeping bone strong at sites where support is needed. When formation and resorption activities are in balance, there is no net gain or loss of bone. When the rate of bone formation by the osteoblasts is faster than that of the osteoclast activity, bone develops into a longer, wider, or denser form. On the other hand, when the osteoclast activity is greater than the osteoblast activity, bone loss will be caused and the bone pores will become large and loose, which finally results in osteoporosis along with systemic bone loss, destruction of bone microstructures and the increased risk of bone fractures.

Osteoporosis has no symptoms; its main consequence is the increased risk of bone fractures. Osteoporotic fractures occur in situations where healthy people would not normally break a bone; they are therefore regarded as fragility fractures.

High-risk groups of osteoporosis include: older, premenopausal or postmenopausal women, or those with smaller body size, thyroid or parathyroid dysfunction, or a family history of osteoporosis. In addition, personal factors (such as excessive drinking, excessive intake of caffeine or carbonated beverages, lack of exercise, insufficient intake of calcium and vitamin D, menstrual abnormalities caused by abnormal diet, long-term use of steroids for such as asthma and rheumatoid arthritis patients) also increase the risk of suffering from osteoporosis.

The current osteoporosis medicines are classified into the following categories according to the bone remodeling mechanism.

1. Anti-Resorptive Drugs

Anti-resorptive drugs include bisphosphonate, RANKL monoclonal antibody and selective estrogen receptor modulators (SERMs) for inhibiting the osteoclasts activity and reducing resorption of bone. The orally administered bisphosphonates include Fosamax® and Reosteo®, but the absorption effect is affected by food. Intravenous bisphosphonates include Bonviva® and Aclasta®, but they may cause the side effects of vomiting, esophageal irritation, cold, fever or muscle aches. In addition, long-term use of bisphosphonates may cause osteonecrosis of the jaw or bone fractures. The RANKL monoclonal antibody, such as denosumab (Prolia®), is injected subcutaneously into osteoporosis patients to mimic the role of osteoprotegerin (OPG). RANKL monoclonal antibody is combined with RANKL to interfere the development of osteoclasts to thus reduce bone loss, but it also has the risk of side effects such as hypocalcemia, skin infection, and osteonecrosis of the jaw. SERMs including Evista® selectively compete with estrogens for binding estrogen receptor and act as an agonist in bone but an antagonist in the breast and endometrium, but SERMs cannot be used for patients with cardiovascular disease because of the possible side effects of hot flashes, deep vein thrombosis, coronary embolism or stroke.

2. Osteogenic Drugs

Recombinant human parathyroid hormone can stimulate osteoblast activity to achieve bone formation. The commercial Teriparatide (Forteo®) can significantly increase bone mass density after treatment, but the effect will be reduced after 18 months of the treatment, and the common side effects include nausea, headache, dizziness, joint pain, leg cramps, etc.

3. Drugs with Hybrid Mechanisms

Such drugs can be used to treat osteoporosis by stimulating bone formation as well as inhibiting bone loss. An example of such drugs is strontium ranelate (Protos®), which is strontium (II) salt of ranelic acid. Strontium has a great affinity for bone because its physical properties are similar to calcium. Strontium ranelate is an agonist of the calcium sensing receptor and promotes bone formation by inducing osteoblast differentiation from osteoblast precursor cells, and reduces bone resorption by stimulating osteoblasts to secrete osteoclast inhibitors to block osteoclast maturation. However, strontium ranelate may have side effects such as diarrhea, headache, dermatitis, gastritis and esophagitis, and may also cause venous thrombosis and coronary embolism.

There is no evidence in clinical trials that the combination of two or more osteoporosis drugs can increase the effectiveness. Therefore, the guidelines for osteoporosis prevention and treatment in the world do not recommend the use of two or more anti-bone loss agents or a combination of an anti-bone loss agent and an osteogenic agent. In view of the fact that the current drugs for osteoporosis have many side effects, drug treatment needs to take more than one year to have a significant effect, and the combination therapy also lacks strong experimental data, so it is necessary to develop novel products to combat bone diseases such as osteoporosis.

Another example of a bone disease is bone defect resulting from trauma, infection (including osteomyelitis), tumor, or various congenital diseases (such as cleft lip and palate, ear defects, nasal defects, etc.). Minor bone defects can heal on their own, but larger bone defects or bone defects on smaller bones will be difficult to heal completely and will require surgical treatments, e.g., bone grafting (including autologous bone grafting, allogeneic bone grafting and xenogeneic bone grafting) and bone transport treatments for such as artificial bone (including bone cement and bioceramic bone) and tissue engineering bone.

For various bone diseases (such as osteoporosis, bone defects, bone fractures, etc.), different drugs or surgical treatments are required. In view of the above, there is an urgent need for novel and progressive techniques to treat bone diseases.

In view of the above, because of the defect in the prior art, the inventors provide the present invention to effectively overcome the demerits in the prior art. The descriptions of the present invention are as follows.

SUMMARY OF EXEMPLARY EMBODIMENTS

The present invention discloses a novel and advanced technique for overcoming the deficiencies of existing drugs for treating bone diseases. Particularly, the present invention discloses a method for preventing, treating or relieving bone diseases by using *Lactobacillus*, a pharmaceutical composition thereof or an edible composition thereof, wherein the use of *Lactobacillus* is effective in increasing blood calcium concentration in a subject.

The present invention discloses a use of *Lactobacillus* in preparing a pharmaceutical composition for preventing, treating or relieving bone diseases, wherein the *Lactobacillus* is effective in increasing blood calcium concentration in a subject. The bone diseases may include, but are not limited to, osteoporosis, bone defects and bone fractures.

The present invention further discloses a use of *Lactobacillus* in preparing an edible composition for preventing, treating or relieving bone diseases, wherein the *Lactobacillus* is effective in increasing blood calcium concentration in a subject.

The present invention further discloses a method for preventing, treating or relieving a bone disease, wherein the method comprises a step of administering to a subject in need thereof an effective amount of a composition to prevent, treat or relieve the bone disease, wherein the composition includes at least one of *Lactobacillus plantarum* GKM3 and *Lactobacillus paracasei* GKS6, and a pharmaceutically acceptable carrier.

In an embodiment, the *Lactobacillus* is *Lactobacillus plantarum* GKM3, *Lactobacillus paracasei* GKS6 or a combination thereof. In an embodiment, the *Lactobacillus* is *Lactobacillus plantarum* GKM3, which is deposited in China General Microbiological Culture Collection Center (CGMCC) with a deposition number of CGMCC 14565 on Aug. 25, 2017 and in Bioresource Collection and Research Center (BCRC) of the Food Industry Research Institute in Taiwan with a deposition number of BCRC 910787. In an embodiment, the *Lactobacillus* is *Lactobacillus paracasei* GKS6, which is deposited in CGMCC with a deposition number of CGMCC 14566 on Aug. 25, 2017 and in BCRC of the Food Industry Research Institute in Taiwan with a deposition number of BCRC 910788.

The present invention further discloses a method for treating a subject diagnosed with a bone disease. The method comprises steps of identifying the subject having the bone disease by known methods in this field, and administering to the subject an effective amount of a composition comprising at least one of *Lactobacillus plantarum* GKM3 and *Lactobacillus paracasei* GKS6. In an embodiment, the subject having the bone disease is identified according to a bone parameter being a blood calcium concentration, a bone volume density (BV/TV), a trabecular number (Tb.N), a trabecular thickness (Tb.Th), a trabecular spacing (Tb.Sp), or a combination thereof, and the composition improves the bone parameter. In an embodiment, the composition reduces one of a pathological effect and a symptom of the bone disease. In an embodiment, the one of the pathological effect and the symptom of the bone disease is at least one of a bone fracture and a decreased blood calcium concentration.

The present invention further discloses a method for treating a calcium deficiency in blood (such as the calcium deficiency disease, hypocalcemia) to prevent, treat or relieve a bone disease. The method comprises a step of administering to a subject with an effective amount of a composition to prevent, treat or relieve the bone disease. The composition includes at least one of *Lactobacillus plantarum* GKM3 and *Lactobacillus paracasei* GKS6 and a pharmaceutically acceptable carrier.

Any edible composition and pharmaceutical composition containing the *Lactobacillus* thereof according to the present invention is capable of achieving an equivalent or similar effect compared to the commercial drugs for treating bone diseases. The bone diseases may be caused by advanced age, menopause, small body size, thyroid or parathyroid dysfunction, history of osteoporosis, excessive drinking, excessive intake of caffeine or carbonated beverages, lack of exercise, insufficient intake of calcium and vitamin D, menstrual abnormalities caused by abnormal diet, and/or long-term use of steroids. The commercial drugs that can be compared to the present invention include, but are not limited to, the anti-resorptive drugs (e.g., bisphosphonate, RANKL monoclonal antibody and SERM), the osteogenic drugs (e.g., Forteo®) and/or drugs with hybrid mechanisms (e.g., Protos®).

In an embodiment according to the present invention, the commercial drug to be compared with the present invention is Fosamax®, also known as alendronate (Alen) or alendronic acid), which is a synthetic analogue of pyrophosphate. Fosamax®, which can bind to hydroxyapatite in bone and act as a specific inhibitor of bone resorption caused by osteoclasts, is commonly used to treat osteoporosis, particularly for menopausal women.

The phrase "blood calcium" as used herein refers to the concentration of calcium in the blood. In general, when the calcium intake in a subject is insufficient, by the regulation from the parathyroid gland, the bone releases calcium into the blood to increase blood calcium concentration, thereby maintaining the balance and physiological actions of the subject. In contrast, when the blood calcium concentration is too high, excess calcium is deposited in the bones or filtered by the kidneys to excrete through the urine.

The term "osteoporosis" as used herein refers to a disease caused by reduced bone mass and enlarged holes in the honeycomb structure of bone, which increases the risk for a broken bone.

The phrase "bone defect" as used herein refers to a disease in which the structural integrity of bones of a subject is destroyed. The common bone defects occur in the tibia. The phrase "bone fracture disease" as used herein refers to the fragmentation or deformation of bones caused directly or indirectly by external forces.

In the process of preparing *Lactobacillus* herein as a pharmaceutical or edible composition, one or more carriers or excipients, particularly pharmaceutically acceptable carriers or excipients, may be added. The carriers or excipients include, but are not limited to, microparticles of cerium oxide powder, sucrose fatty acid ester, crystalline cellulose/sodium carboxymethyl cellulose, calcium monophosphate, starch (e.g., wheat starch, rice starch, corn starch, potato starch, dextrin, cyclodextrin, etc.), sugars (e.g., lactose, glucose, sugar, reduced maltose, starch syrup, oligofructose, emulsified oligosaccharides, etc.), and sugar alcohols (e.g., sorbitol, erythritol, xylitol, lactitol, mannitol, etc.).

In the process of preparing *Lactobacillus* herein as a pharmaceutical or edible composition, one or more additives, particularly pharmaceutically acceptable additives, may be added. The additives include, but are not limited to, functional ingredients, antioxidants, gelatinizer, stabilizers, tackifiers, preservatives, colorants, flavoring agents, and so on. The functional ingredients include, but are not limited to, various vitamins, pantothenic acid, folic acid, biotin, zinc, calcium, magnesium, amino acids, oligosaccharides, propolis, royal jelly, eicosapentaenoic acid (EPA), docosahexenoic acid (DHA), coenzyme Q10, chondroitin, lactic acid bacteria, lactoferrin, isoflavones, prune, chitin, chitosan, glucosamine, and so on. The flavoring agents include, but are not limited to, juice extracts with various fruit flavors, perfumes or essences.

In the process of preparing *Lactobacillus* herein as an edible composition, one or more protective agents may be added. The protective agents include, but are not limited to, trehalose, milk powder, polydextrose, sodium glutamate, pyrophosphate, vitamins and arginine.

The types of the edible composition include bacterial powder, fluid dairy product, concentrated milk, yogurt, sour milk, frozen yogurt, lactic acid bacteria fermented drink, milk powder, ice cream, butter, cheese, soy milk, the fermented soy milk, vegetable juice, fruit juice, sports drink, dessert, jelly, candy, baby food, health food, animal feed, dietary supplement, and so on. Depending on the type of edible composition to be prepared, those of ordinary skill in the art may add other appropriate and common additives to the composition in compliance with legal regulations.

BRIEF DESCRIPTION OF THE DRAWINGS

The above embodiments and advantages of the present invention will become more readily apparent to those ordinarily skilled in the art after reviewing the following detailed descriptions and accompanying drawings.

DETAILED DESCRIPTION OF THE PREFERRED EMBODIMENTS

Figure 1:
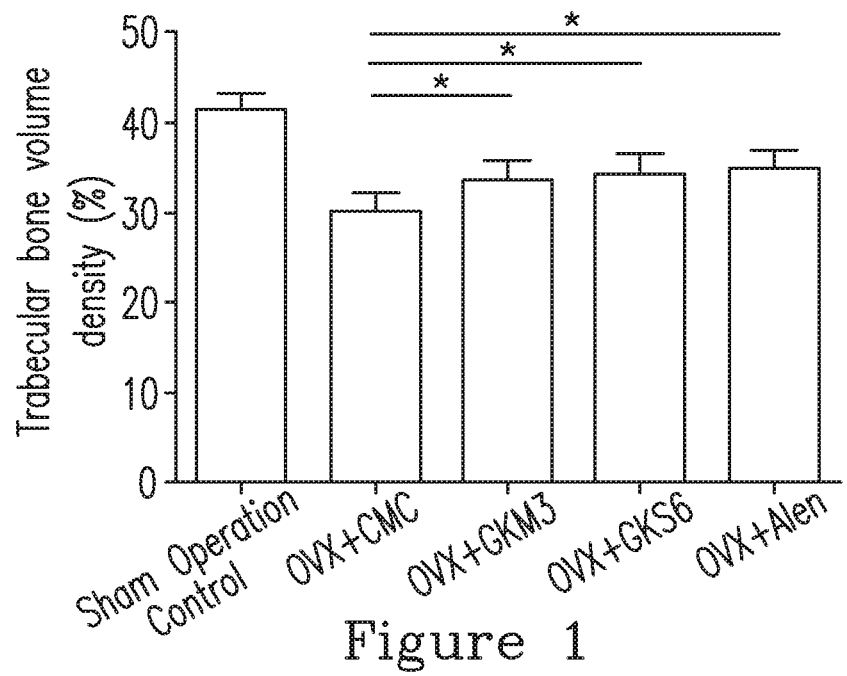
FIG. 1 shows the trabecular bone volume density (%) in the sham operation control group, the ovariectomized control group (the OVX+CMC group), the OVX+GKM3 group, the OVX+GKS6 group, and the OVX+Alen group.

Please refer to all Figures of the present invention when reading the following detailed description, wherein all Figures of the present invention demonstrate different embodiments of the present invention by showing examples, and help the skilled person in the art to understand how to implement the present invention. The present examples provide sufficient embodiments to demonstrate the spirit of the present invention, each embodiment does not conflict with the others, and new embodiments can be implemented through an arbitrary combination thereof, i.e., the present invention is not restricted to the embodiments disclosed in the present specification.

The present invention discloses a method for preventing, treating or relieving bone diseases by using *Lactobacillus*, a pharmaceutical composition thereof or an edible composition thereof, and a use of *Lactobacillus* in preparing a pharmaceutical or edible composition for preventing, treating or relieving bone diseases, wherein the *Lactobacillus* is effective in increasing blood calcium concentration in a subject.

In an embodiment, the species of *Lactobacillus* include, but are not limited to, *L. plantarum, L. paracasei, L. acidophilus, L. brevis, L. casei, L. delbrueckii, L. delbrueckii* subsp. *delbrueckii, L. delbrueckii* subsp. *bulgaricus, L. delbrueckiii* subsp. *lactis, L. rhamnosus, L. salivarius, L. fermentum, L. gasseri, L. helveticus, L. johnsonii, L. pentosus,* and *L. reuteri.*

In an embodiment, the strains of *L. plantarum* include, but are not limited to, *Lactobacillus plantarum* GKM3, which is deposited in China General Microbiological Culture Collection Center (CGMCC) with a deposition number of CGMCC 14565 on Aug. 25, 2017 and in Bioresource Collection and Research Center (BCRC) in Taiwan with a deposition number of BCRC 910787. In an embodiment, the strains of *L. paracasei* include, but are not limited to, *Lactobacillus paracasei* GKS6, which is deposited in CGMCC with a deposition number of CGMCC 14566 on Aug. 25, 2017 and in BCRC in Taiwan with a deposition number of BCRC 910788.

In the pharmaceutical composition or edible composition, there may be one or more species or strains of the *Lactobacillus*. For example, as described in the examples below, *L. plantarum* strain GKM3 is used in a pharmaceutical composition or an edible composition. Alternatively, *L. paracasei* strain GKS6 is used in a pharmaceutical composition or an edible composition. Alternatively, both strains GKM3 and GKS6 are used in a pharmaceutical composition or an edible composition.

In an embodiment, the pharmaceutical composition or the edible composition significantly increases the blood calcium concentration, the trabecular bone volume density (bone volume (BV)/total volume (TV) of the whole examined sample, BV/TV), the trabecular thickness (Tb.Th), the trabecular number (Tb.N) and the bone mineral density (BMD) in a subject. In addition, the pharmaceutical composition or the edible composition decreases trabecular spacing (Tb.Sp) significantly. In an embodiment, the bone diseases include, but are not limited to, osteoporosis, bone defects and bone fractures.

In an embodiment, the edible composition includes, but is not limited to, bacterial powder, fluid dairy product, concentrated milk, yogurt, sour milk, frozen yogurt, lactic acid bacteria fermented drink, milk powder, ice cream, butter, cheese, soy milk, the fermented soy milk, vegetable juice, fruit juice, sports drink, dessert, jelly, candy, baby food, health food, animal feed and dietary supplement.

Source of the Test Substances

*Lactobacillus plantarum* GKM3 (with deposition number of BCRC 910787) and *Lactobacillus paracasei* GKS6 (with deposition number of BCRC 910788) used in the embodiments of the present invention are purchased from Bioresource Collection and Research Center (BCRC) of the Food Industry Research Institute in Taiwan. Those of ordinary skill in the art may also obtain strains of *L. plantarum, L. paracasei* and their subspecies from BCRC or other centers for obtaining microbial strains, such as *L. plantarum* strains with BCRC numbers 10069, 10357, 12327, etc. and *L. paracasei* strains with BCRC numbers 10358, 14628, 17005, etc.

Test Substance Fermentation

Cultivation methods of strains GKM3 and GKS6 are disclosed in Taiwan Patent No. 1636133 (with the application Ser. No. 10/613,6134 and filed on Oct. 20, 2017) and Taiwan Patent No. 1651412 (with the Application No. 106137773 and filed on Nov. 1, 2017), which are incorporated herein in their entirety by reference. The carbon sources used in the medium of the strains GKM3 and GKS6 may include, but are not limited to, glucose, sucrose, lactose, fructose, mannose, sorbitol, glycerin, molasses or a combination thereof, and the amounts of the aforementioned components in the medium may be adjusted as appropriate. In an embodiment, the carbon source is sucrose. The nitrogen sources used for the medium of the strains GKM3 and GKS6 may include, but are not limited to, soy protein, yeast extract, beef extract, casein powder, whey protein powder, the hydrolyzed fish protein, plant extract protein or a combination thereof, and the amounts of the aforementioned components in the medium may be adjusted as appropriate. In an embodiment, the nitrogen source is yeast extract. The amounts of the carbon source and the nitrogen source relative to the total weight of the medium affects the culture result, and are within the range of 1 to 10 weight percentage (wt %), respectively. In an embodiment, either the amount of the carbon source or that of the nitrogen source is 3 wt % to 7 wt %, relative to the total weight of the medium. In an embodiment, the medium contains sucrose and yeast extract at an amount of 1 wt % to 10 wt %, respectively, relative to the total weight of the medium. In an embodiment, the medium contains sucrose and yeast extract at an amount of 3 wt % to 7 wt %, respectively, relative to the total weight of the medium. In an embodiment, the medium contains only one of sucrose and yeast extract at an amount of 1 wt % to 10 wt % or 3 wt % to 7 wt %, relative to the total weight of the medium.

The strains GKM3 and GKS6 can be cultured in a solid medium or a liquid medium at a culture temperature between 32° C. and 42° C. In an embodiment, the culture temperature is set between 35° C. and 40° C. In an embodiment, the culture temperature is 37° C. When the strains GKM3 and GKS6 are cultured in a liquid medium, the rotation speed of the culture vessel or the fermentation tank can be set from 5 rpm to 50 rpm, so that the strains GKM3 and GKS6 are uniformly distributed in the liquid medium, and the gas in the culture vessel or the fermentation tank is appropriately dissolved into the liquid medium. In an embodiment, the rotation speed is in a range between 10 rpm and 35 rpm, or is 20 rpm.

According to the medium and the culture conditions above, the maximum viable cell for the strain GKM3 in the batch fermentation was $4.6 \times 10^9$ colony forming units (CFU)/mL, and that for the strain GKS6 in the batch fermentation was $1.3 \times 10^{10}$ CFU/mL.

The cultured strains GKM3 and GKS6 can be dehydrated by freeze-drying technique and stored as bacterial powders. Protective agents that may be added during the freeze-drying process to produce an edible composition include, but are not limited to, trehalose, milk powder, polydextrose, monosodium glutamate, pyrophosphate, vitamins, arginine or a combination thereof, and the amounts of the aforementioned components in the medium may be adjusted as appropriate.

Alternatively, according to conventional pharmaceutical techniques, the freeze-dried strains GKM3 and GKS6 may be combined with pharmaceutically acceptable carriers, excipients, diluents, adjuvants, vehicles, dispersing agents, coatings, antibacterial or antifungal agents, and prepared as tablets, capsules, granules, pills, tablets, powders, emulsifier, liquid suspension, dispersant, solvent and the like. In view of the above, strains GKM3 and GKS6 can be prepared as bacterial powders, an edible composition or a pharmaceutical composition.

Preparation of Test Substances

The animal experiments in the present invention can be carried out by feeding 10 mg to 2000 mg of GKM3 and GKS6 powders per kg of mouse body weight. However, more than 2000 mg or less than 10 mg of GKM3 and GKS6 powders per kg of mouse body weight is also within the scope of the present invention. For subjects other than mice taking GKM3 or GKS6 powder, their pharmaceutical composition or edible composition, the dosage can be moderately adjusted according to 10~2000 mg/kg body weight of the subject.

In this embodiment, GKM3 and GKS6 powders were each prepared in a 0.5% (w/v) carboxymethylcellulose (CMC) solution as a suspension with a concentration of 205 mg/mL The vehicle group used 0.5% (w/v) CMC solution. For the positive control group, the anti-osteoporosis drug, alendronate (Alen), was prepared as a 0.25 mg/mL suspension in 0.5% (w/v) CMC solution. Mice were tube-fed 0.1 mL of GKM3 suspension, GKS6 suspension, 0.5% (w/v) CMC solution or Alen suspension per 10 g of body weight.

Experimental Animal and Model

Because bone metabolism is closely related to estrogen, mice with bilateral ovariectomy were used as a model for studying osteoporosis in postmenopausal animals. After the recovery period of 1 to 2 weeks after the bilateral ovariectomy, mice were randomly assigned to different treatment groups.

In this embodiment, 8-week-old ICR female mice were purchased from BioLASCO Taiwan Co., Ltd., and ovariectomy (OVX) was performed when they were 9 weeks old. The experimental groups and the positive control group of the mice underwent anesthesia and were ovariectomized through their back for both sides of the ovaries. For the sham operation group, which was used as a control group, ICR mice's abdominal cavities were cut but their ovaries were not removed. When the mice were sacrificed, the ovarian tissues were checked to confirm whether the removal of ovarian was successful. The mice with unsuccessful ovariectomy were not used in the subsequent experiments.

ICR female mice were divided into a sham operation control group and 4 ovariectomized groups (Ovariectomy;

OVX). The 4 ovariectomized groups include the vehicle group (OVX+CMC group), the positive control group (OVX+Alen group, with a dosage of 2.5 mg Alen/kg mouse weight), GKM3 treatment group (OVX+GKM3 group, with a dosage of 205 mg GKM3/kg mouse weight) and GKS6 treatment group (OVX+GKS6 group, with a dosage of 205 mg GKS6/kg mouse weight). GKM3 treatment group and GKS6 treatment group were given the test substance by oral gavage at 4 days after surgery once/day for 28 days. The positive control group was fed alendronate 3 times a week for 28 days. The mice were anesthetized and sacrificed for intraperitoneal cephalic vein sampling, and each femur was removed for analysis.

Bone Tissue Analysis

Computerized tomography images of the right distal femur of ICR mice were obtained by a micro-computed tomography (micro-CT) scanner (SkyScan 1076, Kontizh, Belgium) with a resolution of 18 μm and were analyzed by a software to obtain the trabecular bone volume density (i.e., bone volume/tissue volume, BV/TV), the trabecular thickness (Tb.Th), the trabecular number (Tb.N), and the trabecular spacing (Tb.Sp). The analyzed position was selected to include the area of 100 pieces under the growth plate but not the cortical bone. The bone mineral density analysis was applied to the same area but not the cortical bone.

Bone Density Analysis

The bone density (mass/volume) was detected by the micro-CT. Before the detection, the mice were anesthetized and fixed in a prone position, and then the dual energy X-ray absorptiometry (DXA) was used to scan the examination site. DXA scanner produces two X-ray beams, and measures the number of X-rays that pass through the bone from each beam. The difference between the two beams, the bone mass, bone volume and the bone density, which is also called bone mineral density (BMD), is then calculated.

Statistical Method

The obtained data in the experiments were analyzed with one-way analysis of variance (one-way ANOVA) and the Duncan's multiple range test. All data were presented as mean±SD. After comparisons, the abovementioned groups were analyzed statistically and noted by a mark to represent the statistically significant differences between or among the groups (* represents p<0.05).

Experimental Results

1. Blood Calcium Concentration

When blood calcium concentration is low, which may result from the reduced calcium absorption, the parathyroid hormones (PTH) stimulate cells in the bones to break down and release calcium into the blood, which is not conducive to the increase or maintenance of bone density. Conversely, when calcium concentration rises, the calcitonin in the blood stimulates the skeleton to remove calcium from the blood plasma, and deposit it as bone, which is conducive to the increase or maintenance of bone density. Hypocalcemia, commonly known as a calcium deficiency disease, occurs when calcium levels in the blood are low. A long-term calcium deficiency can lead to osteoporosis.

As shown in Table 1 and Table 2, the blood calcium concentration and the ratio of calcium/creatinine in the mice fed the strains GKM3 and GKS6 were significantly higher than those in the control group (p<0.05), but there was no significant difference in the creatinine concentration. It was reported that the increased serum calcium and calcium/creatinine ratio indicate that the test sample is conducive to calcium absorption. Therefore, based on the results in Tables 1 and 2, the strain GKM3 and/or GKS6 of the present invention and their bacterial powders, the edible composition or the pharmaceutical composition is conducive to calcium absorption.

TABLE 1

Calcium and creatinine concentrations and calcium/creatinine ratio in the blood of female mice of each group

| Groups | Calcium (mg/dL) | Creatinine (mg/dL) | Calcium/Creatinine ratio |
|---|---|---|---|
| Control | 13.5 ± 0.8 | 0.2 ± 0.1 | 67.5 |
| GKM3 | 14.5 ± 0.3* | 0.2 ± 0.0 | 72.5* |
| GKS6 | 15.5 ± 0.6* | 0.2 ± 0.0 | 77.5* |

Values are expressed as mean ± S.E.M. for one-tailed variance analysis (n = 6).
*indicates a statistically significant difference from the control group (p < 0.05).

TABLE 2

Calcium and creatinine concentrations and calcium/creatinine ratio in blood of female mice of each group

| Groups | Calcium (mg/dL) | Creatinine (mg/dL) | Calcium/Creatinine ratio |
|---|---|---|---|
| Control | 13.2 ± 0.6 | 0.2 ± 0.1 | 66 |
| GKM3 | 14.6 ± 0.3* | 0.2 ± 0.0 | 73* |
| GKS6 | 14.7 ± 0.4* | 0.2 ± 0.1 | 73.5* |

Values are expressed as mean ± S.E.M. for one-tailed variance analysis (n = 6).
*indicates a statistically significant difference from the control group (p < 0.05).

2. Trabecular Bone Volume Density

ICR mice were sacrificed on the $32^{nd}$ day after ovariectomy and analyzed for various parameters of the femur. As shown in Table 3 and FIG. 1, the bone volume density of the right femur of the ovariectomized control group (OVX+CMC) mice is significantly smaller than that of the sham operation control group, while the bone volume density of either the OVX+GKM3 group or the OVX+GKS6 group mice is significantly higher than that of the OVX+CMC group (p<0.05) and is close to the OVX+Alen group. This result indicates that the intake of the strains GKM3 and/or GKS6, or the bacterial powder, the edible composition or the pharmaceutical composition thereof according to the present invention is effective in improving a subject's trabecular bone volume density.

TABLE 3

The trabecular bone volume density, which is presented as a % value, in each mice group

| Groups | Trabecular bone volume density (%) |
|---|---|
| Sham operation control group | 41.4 ± 1.7 |
| OVX + CMC group | 30.6 ± 1.7# |
| OVX + GKM3 group | 33.5 ± 2.2* |
| OVX + GKS6 group | 34.2 ± 2.3* |
| OVX + Alen group | 34.9 ± 2.0* |

Values are expressed as mean ± S.E.M. for one-tailed variance analysis (n = 6).
indicates a statistically significant difference from the sham operation control group (p < 0.05).
*indicates a statistically significant difference from the OVX + CMC group (p < 0.05).

3. Femur Trabecular Thickness (Tb.Th)

Figure 2:
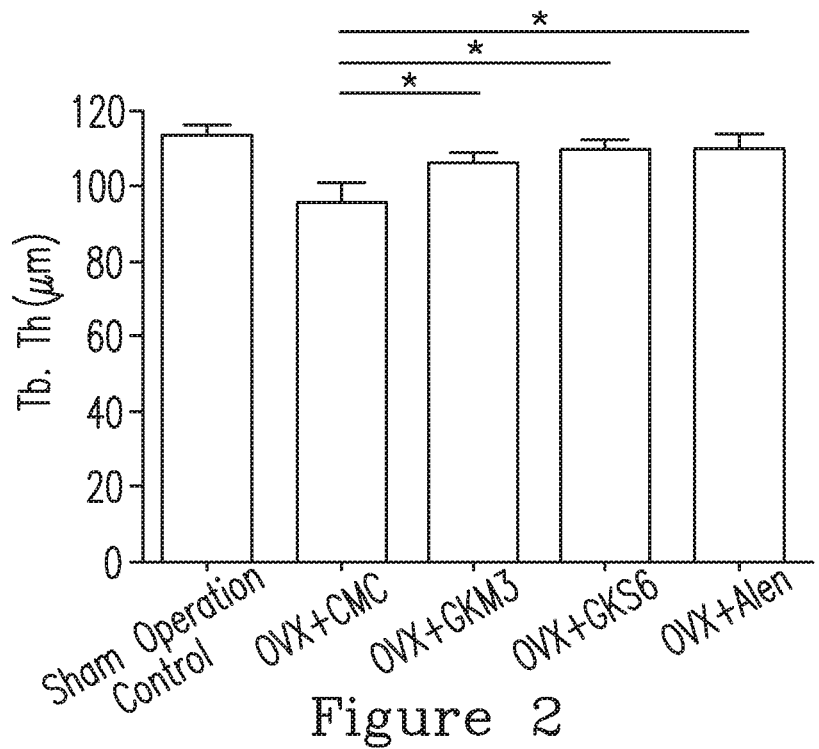
FIG. 2 shows the trabecular thickness (Tb.Th) of the femur in the sham operation control group, the ovariectomized control group (the OVX+CMC group), the OVX+GKM3 group, the OVX+GKS6 group, and the OVX+Alen group.

As shown in Table 4 and FIG. 2, the Tb.Th of the right femur of the ovariectomized control group (OVX+CMC) mice is significantly smaller than that of the sham operation control group, while the Tb.Th of either the OVX+GKM3 group or the OVX+GKS6 group mice is significantly higher than that of the OVX+CMC group (p<0.05) and is close to the OVX+Alen group. This result indicates that the intake of the strains GKM3 and/or GKS6, or the bacterial powder, the edible composition or the pharmaceutical composition thereof according to the present invention is effective in improving the Tb.Th of the femur in a subject.

TABLE 4

The Tb.Th of the femur in each mice group

| Groups | Femur Tb.Th (μm) |
| --- | --- |
| Sham operation control group | 113.7 ± 2.4 |
| OVX + CMC group | 96.7 ± 5.3[#] |
| OVX + GKM3 group | 106.3 ± 2.6* |
| OVX + GKS6 group | 109.8 ± 2.4* |
| OVX + Alen group | 109.9 ± 3.9* |

Values are expressed as mean ± S.E.M. for one-tailed variance analysis (n = 6).
[#]indicates a statistically significant difference from the sham operation control group ($p < 0.05$).
*indicates a statistically significant difference from the OVX + CMC group ($p < 0.05$).

4. Femur Trabecular Number (Tb.N)

Figure 3:
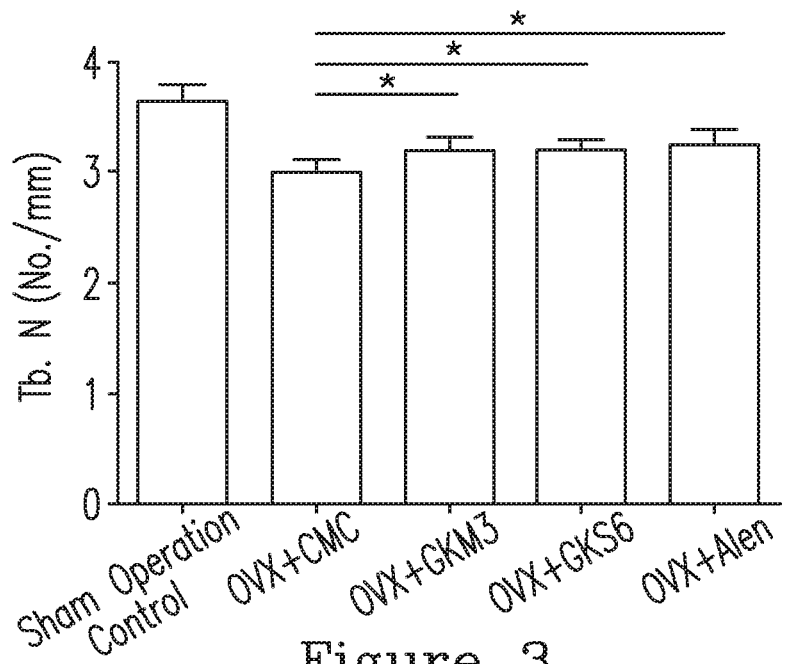
FIG. 3 shows the trabecular number (Tb.N) of the femur in the sham operation control group, the ovariectomized control group (the OVX+CMC group), the OVX+GKM3 group, the OVX+GKS6 group, and the OVX+Alen group.

As shown in Table 5 and FIG. 3, the Tb.N of the right femur of the ovariectomized control group (OVX+CMC) mice is significantly smaller than that of the sham operation control group, while the Tb.N of either the OVX+GKM3 group or the OVX+GKS6 group mice is significantly higher than that of the OVX+CMC group ($p<0.05$) and is close to the OVX+Alen group. This result indicates that the intake of the strains GKM3 and/or GKS6, or the bacterial powder, the edible composition or the pharmaceutical composition thereof according to the present invention is effective in improving the Tb.N of the femur in a subject.

TABLE 5

The Tb.N of the femur in each mice group

| Groups | Femur Tb.N (No./mm) |
| --- | --- |
| Sham operation control group | 3.7 ± 0.2 |
| OVX + CMC group | 3.0 ± 0.1[#] |
| OVX + GKM3 group | 3.2 ± 0.1* |
| OVX + GKS6 group | 3.2 ± 0.1* |
| OVX + Alen group | 3.3 ± 0.1* |

Values are expressed as mean ± S.E.M. for one-tailed variance analysis (n = 6).
[#]indicates a statistically significant difference from the sham operation control group ($p < 0.05$).
*indicates a statistically significant difference from the OVX + CMC group ($p < 0.05$).

5. Femur Trabecular Spacing (Tb.Sp)

Figure 4:
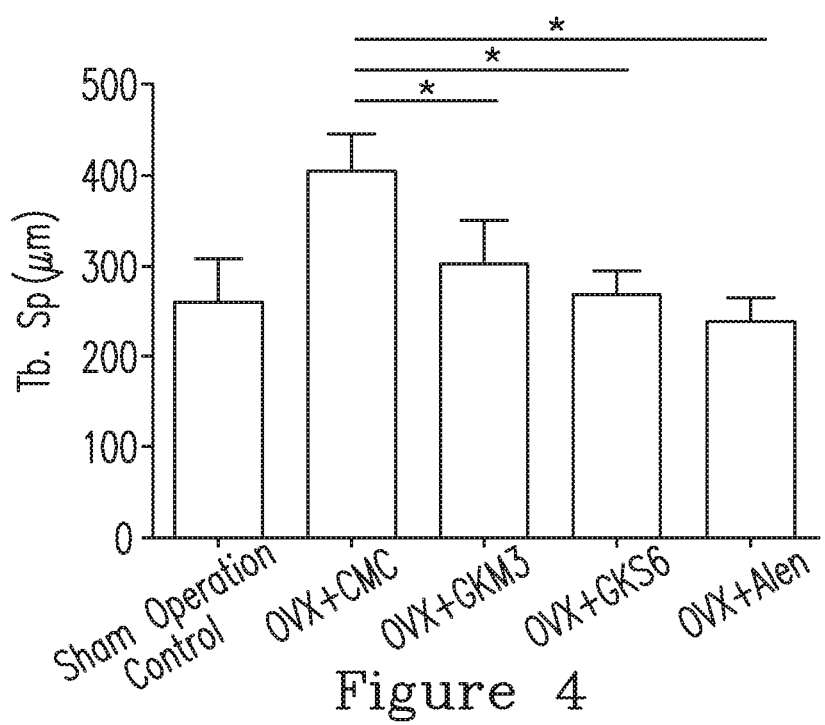
FIG. 4 shows the trabecular spacing (Tb.Sp) of the femur in the sham operation control group, the ovariectomized control group (the OVX+CMC group), the OVX+GKM3 group, the OVX+GKS6 group, and the OVX+Alen group.

As shown in Table 6 and FIG. 4, the Tb.Sp of the right femur of the ovariectomized control group (OVX+CMC) mice is significantly smaller than that of the sham operation control group, while the Tb.Sp of either the OVX+GKM3 group or the OVX+GKS6 group mice is significantly higher than that of the OVX+CMC group ($p<0.05$) and is close to the OVX+Alen group. This result indicates that the intake of the strains GKM3 and/or GKS6, or the bacterial powder, the edible composition or the pharmaceutical composition thereof according to the present invention is effective in improving or reducing a the Tb.Sp of the femur in a subject.

TABLE 6

The Tb.Sp of the femur in each mice group

| Groups | Femur Tb.Sp (μm) |
| --- | --- |
| Sham operation control group | 254.9 ± 47.6 |
| OVX + CMC group | 404.5 ± 40.1[#] |

TABLE 6-continued

The Tb.Sp of the femur in each mice group

| Groups | Femur Tb.Sp (μm) |
| --- | --- |
| OVX + GKM3 group | 300.9 ± 48.8* |
| OVX + GKS6 group | 268.5 ± 26.7* |
| OVX + Alen group | 232.9 ± 25.9* |

Values are expressed as mean ± S.E.M. for one-tailed variance analysis (n = 6).
[#]indicates a statistically significant difference from the sham operation control group ($p < 0.05$).
*indicates a statistically significant difference from the OVX + CMC group ($p < 0.05$).

6. Femur Bone Mineral Density (BMD)

Figure 5:
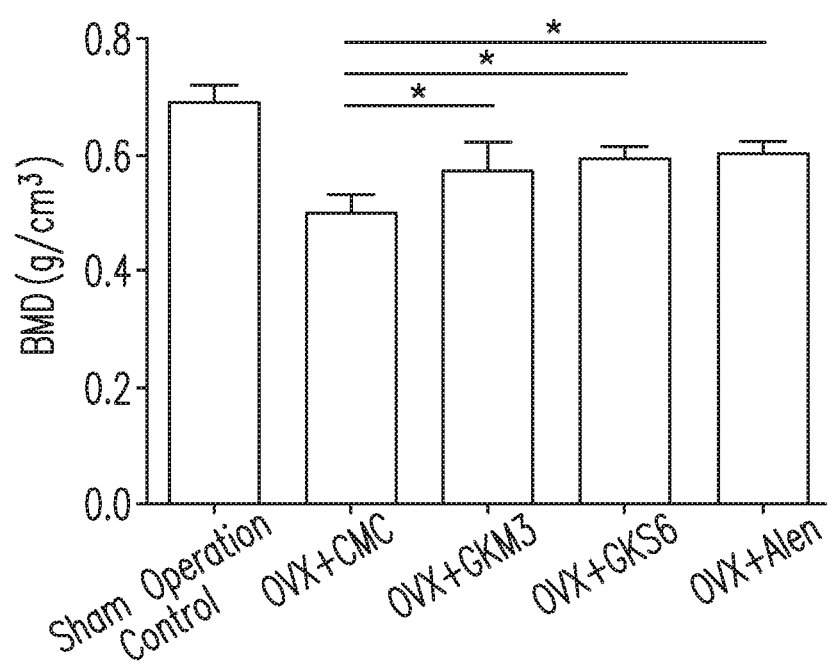
FIG. 5 shows the bone mineral density (BMD) of the femur in the sham operation control group, the ovariectomized control group (the OVX+CMC group), the OVX+GKM3 group, the OVX+GKS6 group, and the OVX+Alen group.

As shown in Table 7 and FIG. 5, the BMD of the right femur of the ovariectomized control group (OVX+CMC) mice is significantly smaller than that of the sham operation control group, while the BMD of either the OVX+GKM3 group or the OVX+GKS6 group mice is significantly higher than that of the OVX+CMC group ($p<0.05$) and is close to the OVX+Alen group. This result indicates that the intake of the strains GKM3 and/or GKS6, or the bacterial powder, the edible composition or the pharmaceutical composition thereof according to the present invention is effective in improving the BMD of a subject.

TABLE 7

BMD of the femur in each mice group

| Groups | Femur BMD (g/cm$^3$) |
| --- | --- |
| Sham operation control group | 0.69 ± 0.03 |
| OVX + CMC group | 0.50 ± 0.03[#] |
| OVX + GKM3 group | 0.57 ± 0.04* |
| OVX + GKS6 group | 0.59 ± 0.02* |
| OVX + Alen group | 0.60 ± 0.02* |

Values are expressed as mean ± S.E.M. for one-tailed variance analysis (n = 6).
[#]indicates a statistically significant difference from the sham operation control group ($p < 0.05$).
*indicates a statistically significant difference from the OVX + CMC group ($p < 0.05$).

Based on the above, the *Lactobacillus* and the composition containing *Lactobacillus* in the present invention can significantly increase the calcium concentration in the blood and the calcium/creatinine ratio of a subject, which is beneficial to the calcium absorption for the subject. In addition, the ovariectomized mice fed with the composition containing *Lactobacillus* in the present invention have significantly increased bone volume density (BV/TV), Tb.Th, Tb.N and BMD and significantly reduced Tb.Sp of the femur. Therefore, the pharmaceutical composition thereof and the edible composition containing the *Lactobacillus* thereof according to the present invention can be used to prevent, treat or relieve bone diseases, particularly osteoporosis, by increasing the calcium concentration in the blood, BV/TV, Tb.Th, Tb.N and BMD and reducing Tb.Sp.

In the present invention, after the mice were fed with the strain GKM3 or GKS6, the calcium concentration in the blood is significantly increased, which promotes deposition of excess calcium into the bone. Therefore, because of the increased bone calcium deposition, the bone diseases of a subject can be treated or relieved, and the risk of suffering from the bone diseases, particularly the osteoporosis, can be reduced.

In the experiments mentioned above, ovariectomized mice can lead to estrogen deficiency, which were used as a model of osteoporosis. Mice are the most commonly used mammalian model organism because they share a high degree of homology with humans. It was proved from numerous experiments and results in this field that the results for rodents (mice) could be applied to other vertebrates, such as mammals. Therefore, the scope to be claimed in the present invention includes vertebrate animals including mammals, which include primates, rodents, and so on. The primates include humans, orangutans, marmosets, monkeys, etc., and the rodents include rats, mice, guinea pigs, and so on. In addition, the scope of application of osteoporosis is not limited to other females with estrogen deficiency. The *Lactobacillus* and the composition containing *Lactobacillus* in the present invention can also be used for males suffering from bone diseases or having a risk of suffering from bone diseases.

Other Embodiments

1. A method for treating a subject diagnosed with a bone disease, comprising steps of identifying the subject having the bone disease, and administering to the subject an effective amount of a composition including at least one of *Lactobacillus plantarum* GKM3 and *Lactobacillus paracasei* GKS6. The *Lactobacillus plantarum* GKM3 is deposited in China General Microbiological Culture Collection Center (CGMCC) with a deposition number of CGMCC 14565 on Aug. 25, 2017, and the *Lactobacillus paracasei* GKS6 is deposited in CGMCC with a deposition number of CGMCC 14566 on Aug. 25, 2017.

2. The method in Embodiment 1, wherein the bone disease is an osteoporosis, a bone defect, a bone fracture, or a combination thereof.

3. The method in Embodiments 1-2, wherein the subject is a human subject.

4. The method in any of Embodiments 1-3, wherein the subject is a menopausal woman.

5. The method in any of Embodiments 1-4, wherein the composition is a pharmaceutical composition.

6. The method in any of Embodiment 5, wherein the pharmaceutical composition further includes a pharmaceutically acceptable carrier.

7. The method in any of Embodiments 1-6, wherein the subject is subject to a once-daily administration, a multiple-daily administration, or a weekly administration.

8. The method in any of Embodiments 1-7, wherein the composition is in a dosage form suitable for oral administration.

9. The method in any of Embodiments 1-8, wherein the dosage form is selected from solutions, suspensions, emulsions, powders, tablets, pills, syrups, lozenges, troches, chewing gums, slurries, or capsules.

10. The method in any of Embodiments 1-9, wherein the composition is a food product, a dietary supplement, or a nutritional product.

11. The method in Embodiment 10, wherein the food product is selected from beverages, yogurt, juices, ice cream, bread, biscuits, cereals, health bars, or spreads.

12. The method in any of Embodiments 1-11, wherein the subject having the bone disease is identified according to a bone parameter being a blood calcium concentration, a bone volume density (BV/TV), a trabecular number (Tb.N), a trabecular thickness (Tb.Th), a trabecular spacing (Tb.Sp), or a combination thereof, and the composition improves the bone parameter.

13. A method for preventing, treating or relieving a bone disease, comprising steps of administering to a subject in need thereof an effective amount of a composition to prevent, treat or relieve the bone disease. The composition includes at least one of *Lactobacillus plantarum* GKM3 and *Lactobacillus paracasei* GKS6, wherein the *Lactobacillus plantarum* GKM3 is deposited in China General Microbiological Culture Collection Center (CGMCC) with a deposition number of CGMCC 14565 on Aug. 25, 2017, and the *Lactobacillus paracasei* GKS6 is deposited in CGMCC with a deposition number of CGMCC 14566 on Aug. 25, 2017.

14. The method in Embodiment 13, wherein the bone disease is an osteoporosis, a bone defect, a bone fracture, or a combination thereof.

15. The method in any of Embodiments 13-14, wherein the composition includes a carrier material.

16. The method in Embodiment 15, wherein the carrier material is selected from oatmeal gruel, lactic acid fermented foods, resistant starch, dietary fibres, carbohydrates, proteins, glycosylated proteins, or lipids.

17. The method in any of Embodiments 13-16, wherein the composition reduces one of a pathological effect and a symptom of the bone disease.

18. The method in Embodiment 17, wherein the one of the pathological effect and the symptom of the bone disease is at least one of a bone fracture and a decreased blood calcium concentration.

19. The method in any of Embodiments 13-18, wherein the composition further includes an edible ingredient.

20. A method for treating a calcium deficiency in blood to prevent, treat or relieve a bone disease, comprising a step of administering to a subject in need thereof an effective amount of a composition to prevent, treat or relieve the bone disease, wherein the composition includes at least one of *Lactobacillus plantarum* GKM3 and *Lactobacillus paracasei* GKS6, and a pharmaceutically acceptable carrier. The *Lactobacillus plantarum* GKM3 is deposited in China General Microbiological Culture Collection Center (CGMCC) with a deposition number of CGMCC 14565 on Aug. 25, 2017, and the *Lactobacillus paracasei* GKS6 is deposited in CGMCC with a deposition number of CGMCC 14566 on Aug. 25, 2017.

While the invention has been described in terms of what is presently considered to be the most practical and preferred embodiments, it is to be understood that the invention need not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A method for treating a subject diagnosed with a bone disease, comprising:
   identifying the subject having the bone disease; and
   administering to the subject an effective amount of a composition including at least one of *Lactobacillus plantarum* GKM3 and *Lactobacillus paracasei* GKS6, wherein the *Lactobacillus plantarum* GKM3 is deposited in China General Microbiological Culture Collection Center (CGMCC) with a deposition number of CGMCC 14565 on Aug. 25, 2017, and the *Lactobacillus paracasei* GKS6 is deposited in CGMCC with a deposition number of CGMCC 14566 on Aug. 25, 2017.

2. The method as claimed in claim 1, wherein the bone disease is an osteoporosis, a bone defect, a bone fracture, or a combination thereof.

3. The method as claimed in claim 1, wherein the subject is a human subject.

4. The method as claimed in claim 1, wherein the subject is a menopausal woman.

5. The method as claimed in claim 1, wherein the composition is a pharmaceutical composition.

6. The method as claimed in claim 5, wherein the pharmaceutical composition further includes a pharmaceutically acceptable carrier.

7. The method as claimed in claim 1, wherein the subject is subject to a once-daily administration, a multiple-daily administration, or a weekly administration.

8. The method as claimed in claim 1, wherein the composition is in a dosage form suitable for oral administration.

9. The method as claimed in claim 8, wherein the dosage form is selected from solutions, suspensions, emulsions, powders, tablets, pills, syrups, lozenges, troches, chewing gums, slurries, and capsules.

10. The method as claimed in claim 1, wherein the composition is a food product, a dietary supplement, or a nutritional product.

11. The method as claimed in claim 10, wherein the food product is selected from beverages, yogurt, juices, ice cream, bread, biscuits, cereals, health bars, and spreads.

12. The method as claimed in claim 1, wherein the subject having the bone disease is identified according to a bone parameter being a blood calcium concentration, a bone volume density (BV/TV), a trabecular number (Tb.N), a trabecular thickness (Tb.Th), a trabecular spacing (Tb.Sp), or a combination thereof, and the composition improves the bone parameter.

13. A method for treating or relieving a bone disease, comprising:
administering to a subject in need thereof an effective amount of a composition to treat or relieve the bone disease, wherein the composition includes at least one of *Lactobacillus plantarum* GKM3 and *Lactobacillus paracasei* GKS6, wherein the *Lactobacillus plantarum* GKM3 is deposited in China General Microbiological Culture Collection Center (CGMCC) with a deposition number of CGMCC 14565 on Aug. 25, 2017, and the *Lactobacillus paracasei* GKS6 is deposited in CGMCC with a deposition number of CGMCC 14566 on Aug. 25, 2017.

14. The method as claimed in claim 13, wherein the bone disease is an osteoporosis, a bone defect, a bone fracture, or a combination thereof.

15. The method as claimed in claim 13, wherein the composition includes a carrier material.

16. The method as claimed in claim 15, wherein the carrier material is selected from oatmeal gruel, lactic acid fermented foods, resistant starch, dietary fibres, carbohydrates, proteins, glycosylated proteins, and lipids.

17. The method as claimed in claim 13, wherein the composition reduces one of a pathological effect and a symptom of the bone disease.

18. The method as claimed in claim 17, wherein the one of the pathological effect and the symptom of the bone disease is at least one of a bone fracture and a decreased blood calcium concentration.

19. The method as claimed in claim 13, wherein the composition further includes an edible ingredient.

20. A method for treating a calcium deficiency in blood to treat or relieve a bone disease, comprising:
administering to a subject in need thereof an effective amount of a composition to treat or relieve the bone disease, wherein the composition includes:
at least one of *Lactobacillus plantarum* GKM3 and *Lactobacillus paracasei* GKS6; and
a pharmaceutically acceptable carrier, wherein the *Lactobacillus plantarum* GKM3 is deposited in China General Microbiological Culture Collection Center (CGMCC) with a deposition number of CGMCC 14565 on Aug. 25, 2017, and the *Lactobacillus paracasei* GKS6 is deposited in CGMCC with a deposition number of CGMCC 14566 on Aug. 25, 2017.

* * * * *